US011259884B2

(12) United States Patent
Burbank

(10) Patent No.: US 11,259,884 B2
(45) Date of Patent: Mar. 1, 2022

(54) ROBOTIC SURGICAL STAPLER ASSEMBLY CONFIGURED TO USE STAPLER RELOAD

(71) Applicant: Intuitive Surgical Operations, Inc., Sunnyvale, CA (US)

(72) Inventor: William A. Burbank, Sandy Hook, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 251 days.

(21) Appl. No.: 16/346,561

(22) PCT Filed: Nov. 2, 2017

(86) PCT No.: PCT/US2017/059706
§ 371 (c)(1),
(2) Date: May 1, 2019

(87) PCT Pub. No.: WO2018/085529
PCT Pub. Date: May 11, 2018

(65) Prior Publication Data
US 2019/0262088 A1  Aug. 29, 2019

Related U.S. Application Data

(60) Provisional application No. 62/416,454, filed on Nov. 2, 2016.

(51) Int. Cl.
*A61B 34/35* (2016.01)
*A61B 34/37* (2016.01)
(Continued)

(52) U.S. Cl.
CPC ........ *A61B 34/35* (2016.02); *A61B 17/07207* (2013.01); *A61B 34/30* (2016.02);
(Continued)

(58) Field of Classification Search
CPC ........ A61B 2017/00367; A61B 17/068; A61B 2017/2902; A61B 2017/2927;
(Continued)

(56) References Cited

U.S. PATENT DOCUMENTS

| 5,792,165 A | 8/1998 | Klieman et al. |
| 2011/0118754 A1* | 5/2011 | Dachs, II .............. H04W 88/12 |
| | | 606/130 |

(Continued)

FOREIGN PATENT DOCUMENTS

| CN | 101400308 A | 4/2009 |
| CN | 101767130 A | 7/2010 |

(Continued)

OTHER PUBLICATIONS

Balasubramaniam M et al., "An Anti Backlash Two-part Shaft Coupling with Interlocking Elastically Averaged Teeth," Precision Engineering, Jul. 2002, 29 pages.

(Continued)

*Primary Examiner* — Kathleen S Holwerda
*Assistant Examiner* — Uyen N Vo
(74) *Attorney, Agent, or Firm* — Jones Robb, PLLC

(57) ABSTRACT

A robotic surgical assembly includes a drive assembly and a shaft assembly. The drive assembly is detachably mountable to a surgical robot and includes roll, pitch, and clamp/fire inputs configured to drivingly couple with respective outputs of the surgical robot. The shaft assembly is mounted to the drive assembly and configured to detachably couple with a stapler reload assembly that includes a reload roll shaft, a reload pitch shaft, and a reload clamp/fire shaft. The shaft assembly includes a roll shaft, a pitch shaft, and a clamp/fire shaft. The roll shaft is drivingly coupled with the roll input and configured to detachably couple to the reload roll shaft. The pitch shaft is drivingly coupled with the pitch (Continued)

input and configured to detachably couple to the reload pitch shaft. The clamp/fire shaft is drivingly coupled with the clamp/fire input and configured to detachably couple to the reload clamp/fire shaft.

15 Claims, 18 Drawing Sheets

(51) Int. Cl.
*A61B 17/072* (2006.01)
*A61B 34/30* (2016.01)
*A61B 17/00* (2006.01)
*A61B 17/29* (2006.01)
*A61B 17/068* (2006.01)

(52) U.S. Cl.
CPC ............ *A61B 34/37* (2016.02); *A61B 17/068* (2013.01); *A61B 2017/00367* (2013.01); *A61B 2017/00473* (2013.01); *A61B 2017/00477* (2013.01); *A61B 2017/2902* (2013.01); *A61B 2017/294* (2013.01); *A61B 2017/2927* (2013.01); *A61B 2017/2929* (2013.01); *A61B 2017/2931* (2013.01); *A61B 2017/2936* (2013.01); *A61B 2017/2943* (2013.01); *A61B 2034/302* (2016.02)

(58) Field of Classification Search
CPC .... A61B 2017/2931; A61B 2017/2936; A61B 2017/294; A61B 2017/2943; A61B 2017/00477; A61B 2017/2929; A61B 2017/07214; A61B 2017/072; A61B 34/35; A61B 34/30; A61B 34/37; A61B 17/07207; A61B 2034/302
See application file for complete search history.

(56) References Cited

U.S. PATENT DOCUMENTS

| | | |
|---|---|---|
| 2011/0264114 A1 | 10/2011 | Choi et al. |
| 2011/0290853 A1 | 12/2011 | Shelton, IV et al. |
| 2011/0290855 A1 | 12/2011 | Moore et al. |
| 2012/0150154 A1* | 6/2012 | Brisson ................. A61B 34/71 606/1 |
| 2012/0292367 A1* | 11/2012 | Morgan ............... A61B 17/105 227/175.1 |
| 2013/0110129 A1* | 5/2013 | Reid ..................... A61B 34/30 606/130 |
| 2014/0221987 A1 | 8/2014 | Jeong et al. |
| 2014/0276720 A1 | 9/2014 | Parihar et al. |

FOREIGN PATENT DOCUMENTS

| | | |
|---|---|---|
| CN | 102440813 A | 5/2012 |
| CN | 103989495 A | 8/2014 |
| CN | 104023652 A | 9/2014 |
| CN | 104337557 A | 2/2015 |
| EP | 1917929 A1 | 5/2008 |
| EP | 2005906 A2 | 12/2008 |
| EP | 2881049 A1 | 6/2015 |
| WO | WO-2012068156 A2 | 5/2012 |
| WO | WO-2012166503 A1 | 12/2012 |
| WO | WO-2014004292 A2 | 1/2014 |
| WO | WO-2014066044 A1 | 5/2014 |
| WO | WO-2015142794 A1 | 9/2015 |

OTHER PUBLICATIONS

Office Action dated Dec. 28, 2020 for Chinese Application No. CN201780067655 filed Nov. 2, 2017, 20 pages.

International Search Report and Written Opinion for Application No. PCT/US2017/059706, dated May 9, 2018, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP17867004.8, dated Jun. 3, 2020, 12 pages.

* cited by examiner

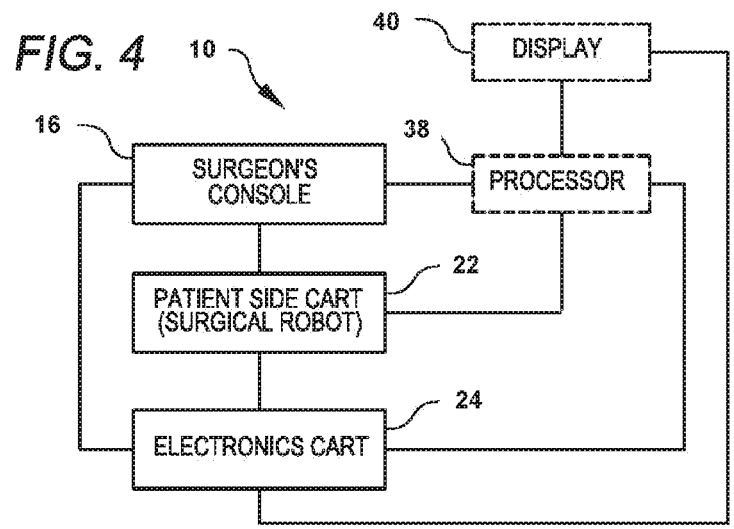
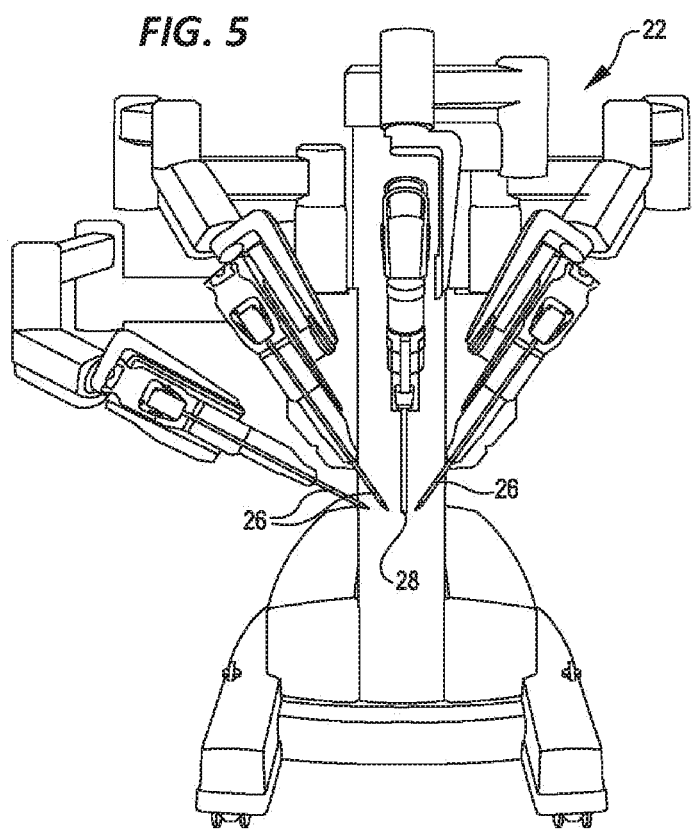

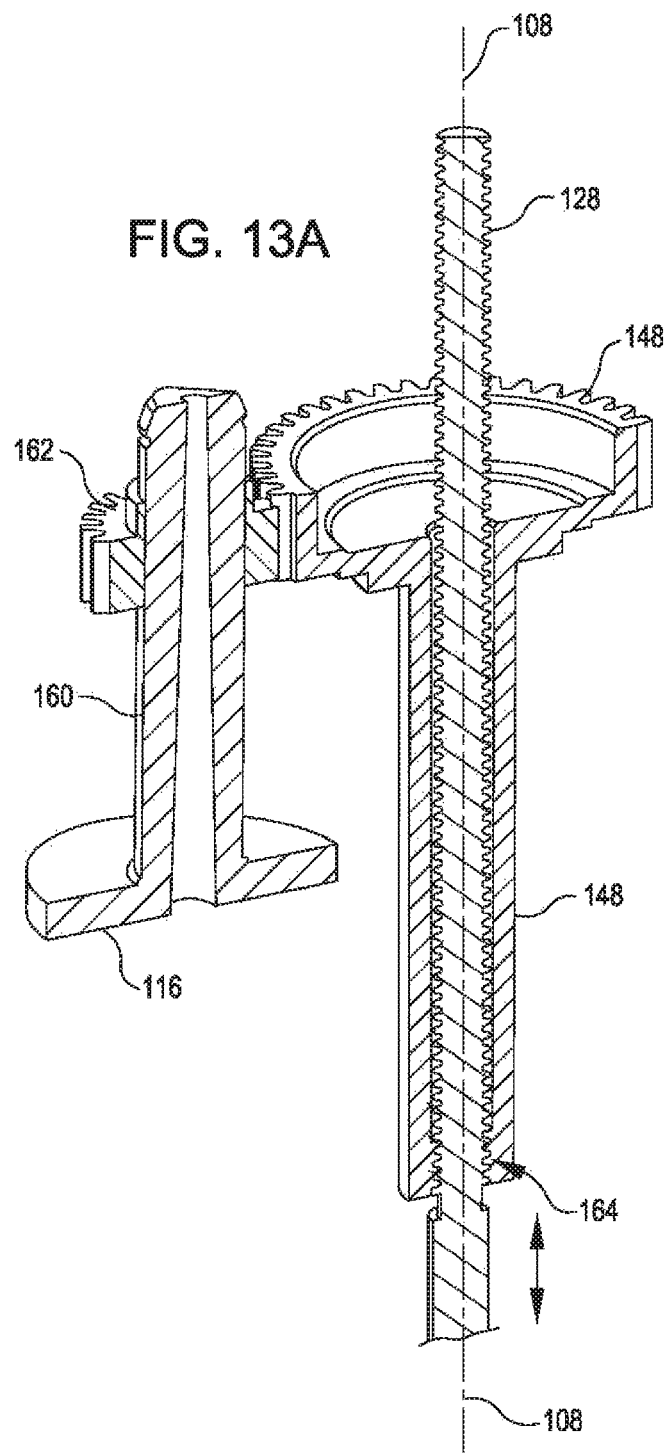

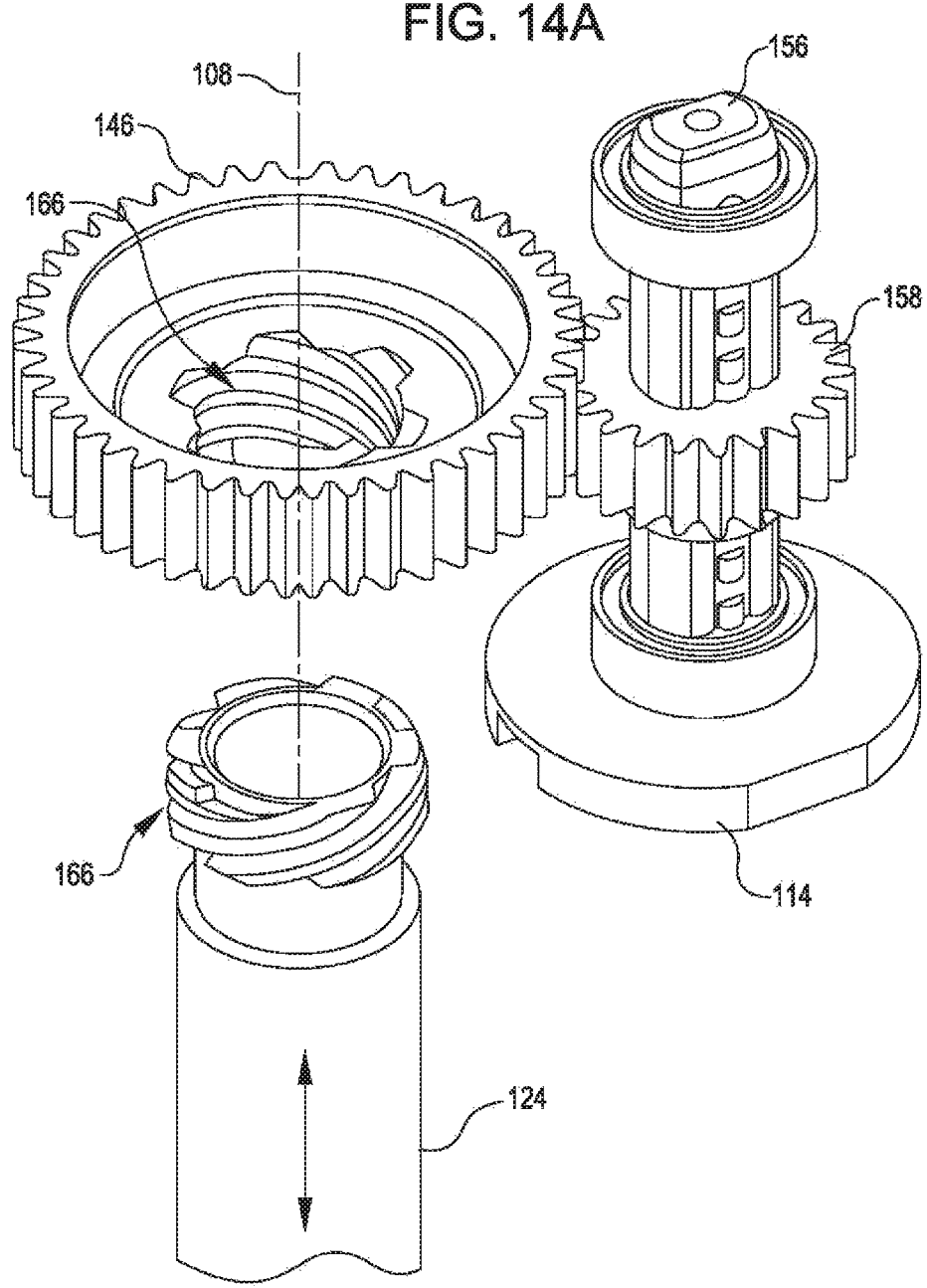

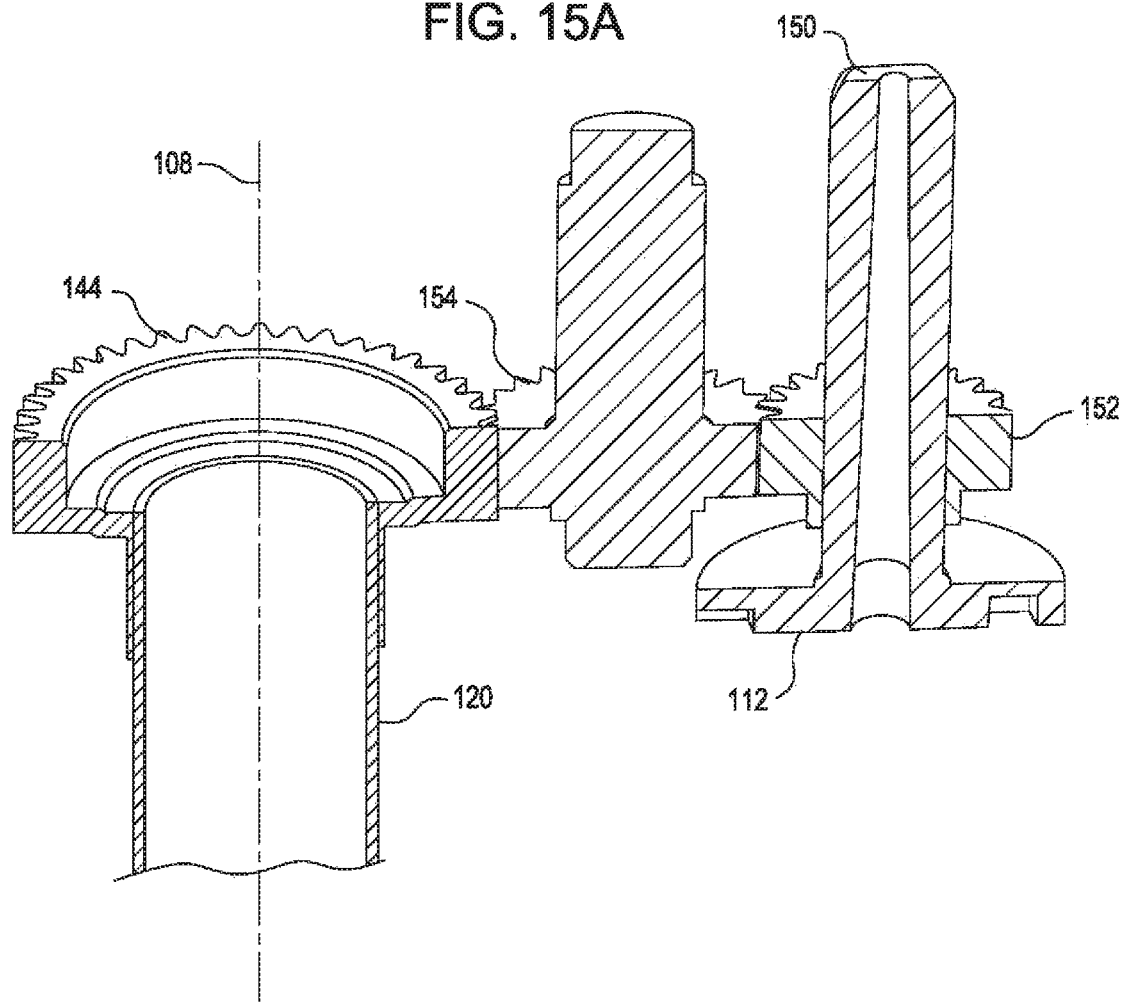

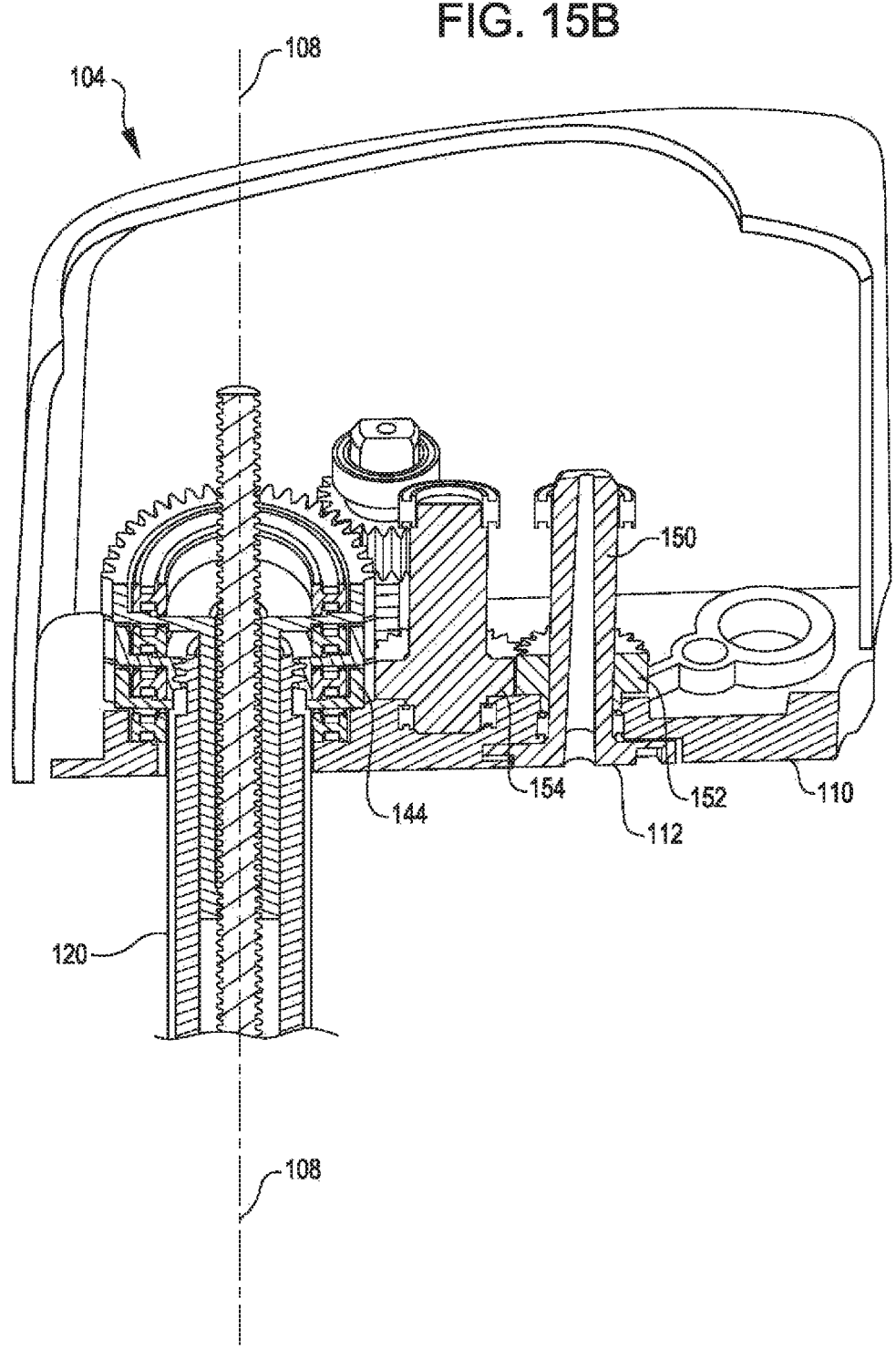

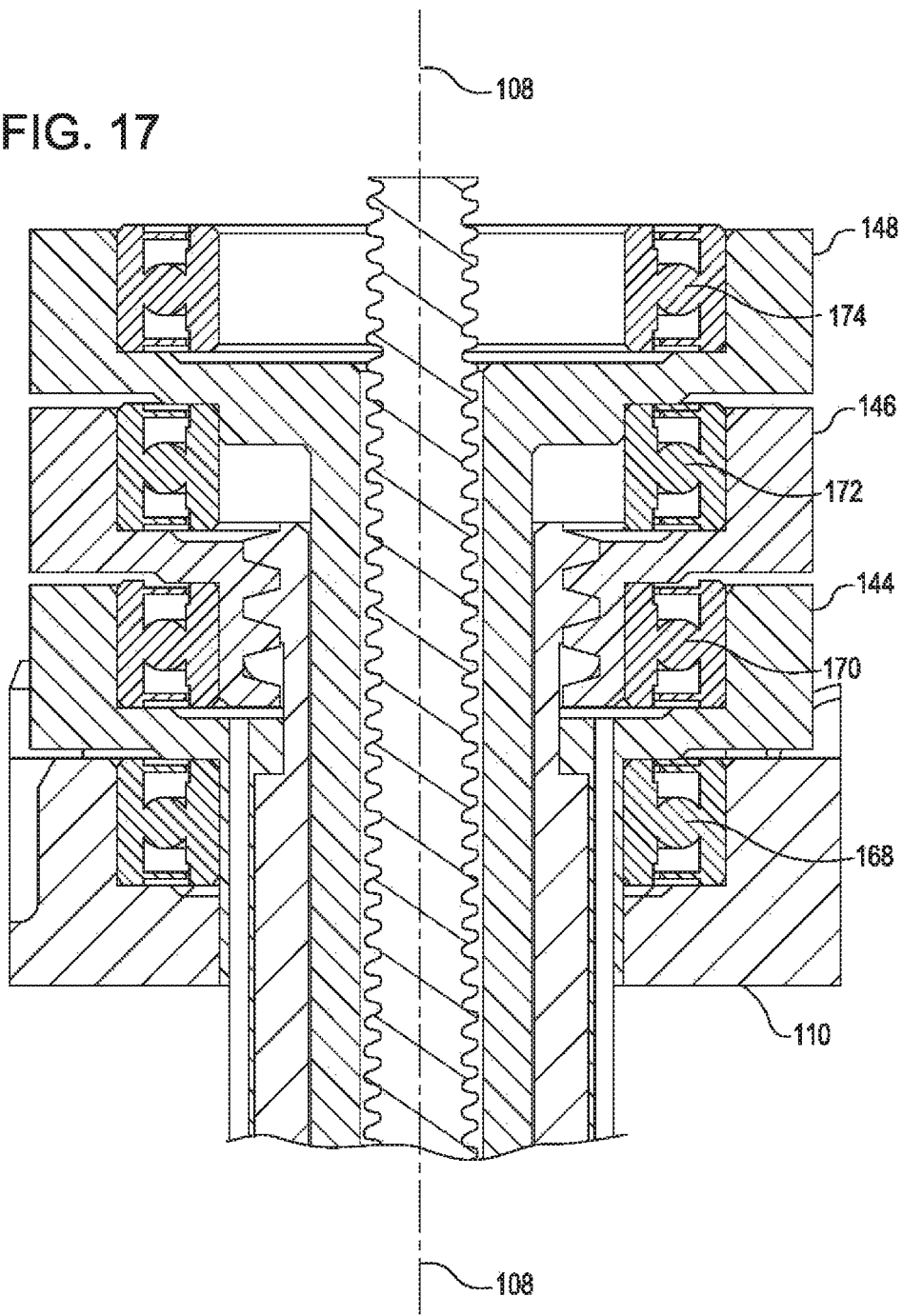

ROBOTIC SURGICAL STAPLER ASSEMBLY CONFIGURED TO USE STAPLER RELOAD

CROSS REFERENCE TO RELATED APPLICATIONS

The present application is a US National Stage application of PCT/US2017/059706 filed Nov. 2, 2017; which claims the benefit of U.S. Provisional Appln. No. 62/416,454 filed Nov. 2, 2016; the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

Surgical staplers are often configured to use a replaceable single use stapler cartridge. A hospital can have a number of different types (e.g., different makes and models) of surgical staplers, including different hand-held surgical staplers and/or telesurgical robotic system surgical staplers. Each type of surgical stapler, however, may be configured to use a corresponding type of stapler cartridge, thereby resulting in a hospital having to stock different types of replaceable stapler cartridges. Stocking different types of replaceable stapler cartridges results in additional expense in terms of additional inventory and resources to ensure that suitable numbers of each type of stapler cartridge are stocked.

BRIEF SUMMARY

Robotic surgical assemblies detachably mountable to a surgical robot are configured to use a replaceable stapler cartridge of a common hand-held surgical stapler. The ability to use the same replaceable stapler cartridge as the common hand-held surgical stapler can help to reduce the number and types of stapler cartridges that are stocked by a hospital, thereby reducing related expense. The use of the same stapler cartridge as the common hand-held surgical stapler can also reduce training expense and help to reduce surgical error related to having to use different types of replaceable stapler cartridges.

Thus, in one aspect, a robotic surgical assembly includes a drive assembly detachably mountable to a surgical robot and a shaft assembly mounted to the drive assembly. The drive assembly includes a chassis, a roll input configured to drivingly couple with a roll output of the surgical robot, a pitch input configured to drivingly couple with a pitch output of the surgical robot, and a clamp/fire input configured to drivingly couple with a clamp/fire output of the surgical robot. The shaft assembly is elongated along a shaft axis and configured to detachably couple with a stapler reload assembly that includes an end effector operable to clamp and staple tissue, a reload roll shaft to which the end effector is pivotally mounted, a reload pitch shaft translatable along the shaft axis to reorient the end effector relative to the reload roll shaft, and a reload clamp/fire shaft drivingly coupled with the end effector and translatable along the shaft axis to actuate the end effector to clamp and staple tissue. The shaft assembly includes a roll shaft, a pitch shaft, and a clamp/fire shaft. The roll shaft is drivingly coupled with the drive assembly so that rotation of the roll input rotates the roll shaft around the shaft axis. The roll shaft has a proximal portion configured to detachably couple to the reload roll shaft. The pitch shaft is drivingly coupled with the drive assembly so that rotation of the pitch input translates the pitch shaft along the shaft axis. The pitch shaft has a proximal portion configured to detachably couple to the reload pitch shaft. The clamp/fire shaft is drivingly coupled with the drive assembly so that rotation of the clamp/fire input translates the clamp/fire shaft along the shaft axis. The clamp/fire shaft has a proximal portion configured to detachably couple to the reload clamp/fire shaft.

In many embodiments of the robotic surgical assembly, the roll shaft, the pitch shaft, and the clamp/fire shaft are coaxial with the shaft axis. For example, the roll shaft can have a roll shaft lumen extending along the shaft axis. The pitch shaft can be accommodated within the roll shaft lumen and constrained to rotate with the roll shaft around the shaft axis. The pitch shaft can have a pitch shaft lumen extending along the shaft axis. The clamp/fire shaft can be accommodated within the pitch shaft lumen and constrained to rotate with the roll shaft around the shaft axis.

In many embodiments of the robotic surgical assembly, the drive assembly includes output gears that are constrained to rotate around the shaft axis. For example, the drive assembly can include a roll output gear drivingly coupled with the roll input. The roll output gear can be attached to the roll shaft and constrained to rotate around the shaft axis. The drive assembly can include a pitch output gear drivingly coupled with the pitch input and constrained to rotate around the shaft axis. The pitch output gear can be drivingly coupled with the pitch shaft via a screw thread interface that converts rotation of the pitch output gear into translation of the pitch shaft along the shaft axis. The drive assembly can include a clamp/fire output gear drivingly coupled with the clamp/fire input and constrained to rotate around the shaft axis. The clamp/fire output gear can be drivingly coupled with the clamp/fire shaft via a screw thread interface that converts rotation of the clamp/fire output gear into translation of the clamp/fire shaft along the shaft axis.

In many embodiments of the robotic surgical assembly, the drive assembly includes output bearings configured to constrain the output gears to rotate around the shaft axis. For example, the drive assembly can include a shaft bearing having an outer race interfaced with the chassis and an inner race interfaced with the roll output gear. The shaft bearing can be configured to constrain the roll output gear to rotation around the shaft axis. The drive assembly can include a roll output gear bearing having an outer race interfaced with the roll output gear and an inner race interfaced the pitch output gear. The roll output gear bearing can be configured to constrain the pitch output gear to rotation around the shaft axis. The drive assembly can include a pitch output gear bearing having an outer race interfaced with the pitch output gear and an inner race interfaced with the clamp/fire output gear. The pitch output gear roller bearing can be configured to constrain the clamp/fire output gear to rotation around the shaft axis. The drive assembly can include an upper chassis supported by the chassis and a clamp/fire output gear bearing having an inner race interfaced with the upper chassis and an outer race interfaced with the clamp/fire output gear. The upper chassis can be detachably mountable to the chassis.

In embodiments of the robotic surgical assembly that include output gears, the output gears are drivingly coupled with the roll input, the pitch input, and the clamp/fire input. For example, the drive assembly can include: (a) a clamp/fire input shaft rotationally coupled with the clamp/fire input; (b) a clamp/fire input gear rotationally coupled with the clamp/fire input shaft, the clamp/fire input gear having external gear teeth drivingly engaging external gear teeth of the clamp/fire output gear; and (c) clamp/fire input shaft bearings, each of the clamp/fire input shaft bearings having an outer race interfaced with the chassis and an inner race interfaced with the clamp/fire input shaft. The drive assembly can include: (a) a pitch input shaft rotationally coupled with the pitch input; (b) a pitch input gear rotationally coupled with the pitch input shaft, the pitch input gear having external gear teeth drivingly engaging external gear teeth of the pitch output gear; and (c) pitch input shaft bearings, each of the pitch input shaft bearings having an outer race interfaced with the chassis and an inner race interfaced with the pitch input shaft. The drive assembly can include: (a) a roll input shaft rotationally coupled with the roll input; (b) roll input shaft bearings, each of the roll input shaft bearings having an outer race interfaced with the chassis and an inner race interfaced with the roll input shaft; (c) a roll input gear rotationally coupled with the roll input shaft; and (d) an idler gear having external teeth drivingly engaged by external teeth of the roll input gear and drivingly engaging external teeth of the roll output gear.

In another aspect, a robotic surgical method of actuating a stapler reload assembly is provided. The method includes detachably mounting a drive assembly of a robotic surgical assembly to a surgical robot so as to: (a) interface a roll output of the surgical robot with a roll input of the drive assembly; (b) interface a pitch output of the surgical robot with a pitch input of the drive assembly; and (c) interface a clamp/fire output of the surgical robot with a clamp/fire input of the drive assembly. The method further includes detachably mounting a stapler reload assembly to a distal end of a shaft assembly of the robotic surgical assembly so as to: (a) interface a roll shaft of the robotic surgical assembly with a roll shaft of the stapler reload assembly; (b) interface a pitch shaft of the robotic surgical assembly with a pitch shaft of the stapler reload assembly; and (c) interface a clamp/fire shaft of the robotic surgical assembly with a clamp/fire shaft of the stapler reload assembly. The roll shaft of the shaft assembly is rotated by actuating a roll shaft drive mechanism drivingly coupling the roll shaft of the shaft assembly with the roll input of the drive assembly by rotating the roll output of the surgical robot. The pitch shaft of the shaft assembly is translated relative to the stapler reload assembly by actuating a pitch shaft drive mechanism drivingly coupling the pitch shaft of the shaft assembly with the pitch input of the drive assembly by rotating the pitch output of the surgical robot. The clamp/fire shaft of the shaft assembly is translated relative to the stapler reload assembly by actuating a pitch shaft drive mechanism drivingly coupling the clamp/fire shaft of the shaft assembly with the pitch input of the drive assembly by rotating the pitch output of the surgical robot.

In many embodiments of the robotic surgical method of actuating a stapler reload assembly, rotating the roll shaft of the shaft assembly includes rotating a roll output gear drivingly coupled with the roll input and attached to the roll shaft. For example, rotating the roll output gear can include: (a) rotating a roll input shaft rotationally coupled with the roll input, (b) rotating a roll input gear rotationally coupled with the roll input shaft, (c) interfacing external gear teeth of the roll input gear with external gear teeth of the roll idler gear, and (d) interfacing external gear teeth of the roll idler gear with external gear teeth of the roll output gear. Rotating the roll output gear can include: (a) interfacing an outer race of a shaft bearing with a chassis of the drive assembly, (b) interfacing an inner race of the shaft bearing with the roll output gear, and (c) rotating the inner race of the shaft bearing with the roll output gear.

In many embodiments of the robotic surgical method of actuating a stapler reload assembly, translating the pitch shaft of the shaft assembly includes: (a) rotating a pitch output gear drivingly coupled with the pitch input, and (b) generating translation of the pitch shaft from rotation of the pitch output gear via a screw thread interface between the pitch shaft and the pitch output gear. For example, rotating the pitch output gear can include: (a) rotating a pitch input shaft rotationally coupled with the pitch input, (b) rotating a pitch input gear rotationally coupled with the pitch input shaft, and (c) interfacing external gear teeth of the pitch input gear with external gear teeth of the pitch output gear. Rotating the pitch output gear can include: (a) interfacing an outer race of a roll output gear bearing with the roll output gear, (b) interfacing an inner race of the roll output gear bearing with the pitch output gear, (c) rotating the inner race of the roll output gear bearing with the pitch output gear, and (d) rotating the outer race of the roll output gear bearing with the roll output gear.

In many embodiments of the robotic surgical method of actuating a stapler reload assembly, translating the clamp/fire shaft of the shaft assembly includes: rotating a clamp/fire output gear drivingly coupled with the clamp/fire input, and (b) generating translation of the clamp/fire shaft from rotation of the clamp/fire output gear via a screw thread interface between the clamp/fire shaft and the clamp/fire output gear. For example, rotating the clamp/fire output gear can include: (a) rotating a clamp/fire input shaft rotationally coupled with the clamp/fire input, (b) rotating a clamp/fire input gear rotationally coupled with the clamp/fire input shaft, and (c) interfacing external gear teeth of the clamp/fire input gear with external gear teeth of the clamp/fire output gear. Rotating the clamp/fire output gear can include: (a) interfacing an outer race of a pitch output gear bearing with the pitch output gear, (b) interfacing an inner race of the pitch output gear bearing with the clamp/fire output gear, (c) rotating the inner race of the pitch output gear bearing with the clamp/fire output gear, and (d) rotating the outer race of the pitch output gear bearing with the pitch output gear. Rotating the clamp/fire output gear can include: (a) interfacing an outer race of a clamp/fire output gear bearing with the clamp/fire output gear, (b) interfacing an inner race of the clamp/fire output gear bearing with an upper chassis of the drive assembly supported by the chassis of the drive assembly, and (c) rotating the outer race of the clamp/fire output gear bearing with the clamp/fire output gear.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4 diagrammatically illustrates a robotic surgery system, in accordance with many embodiments.

FIG. 5 is a front view of a patient side cart (surgical robot) of a robotic surgery system, in accordance with many embodiments.

FIG. 13A and FIG. 13B illustrate components of the drive assembly of the surgical stapler base assembly of FIG. 8 for generating translation of a clamp/fire shaft, in accordance with many embodiments.

FIG. 14A and FIG. 14B illustrate components of the drive assembly of the surgical stapler base assembly of FIG. 8 for generating translation of a pitch shaft, in accordance with many embodiments.

FIG. 15A, FIG. 15B, and FIG. 16 illustrate components of the drive assembly of the surgical stapler base assembly of FIG. 8 for generating rotation of a roll shaft, in accordance with many embodiments.

FIG. 17 is a cross-sectional view through an output gear assembly of the surgical stapler base of FIG. 8, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
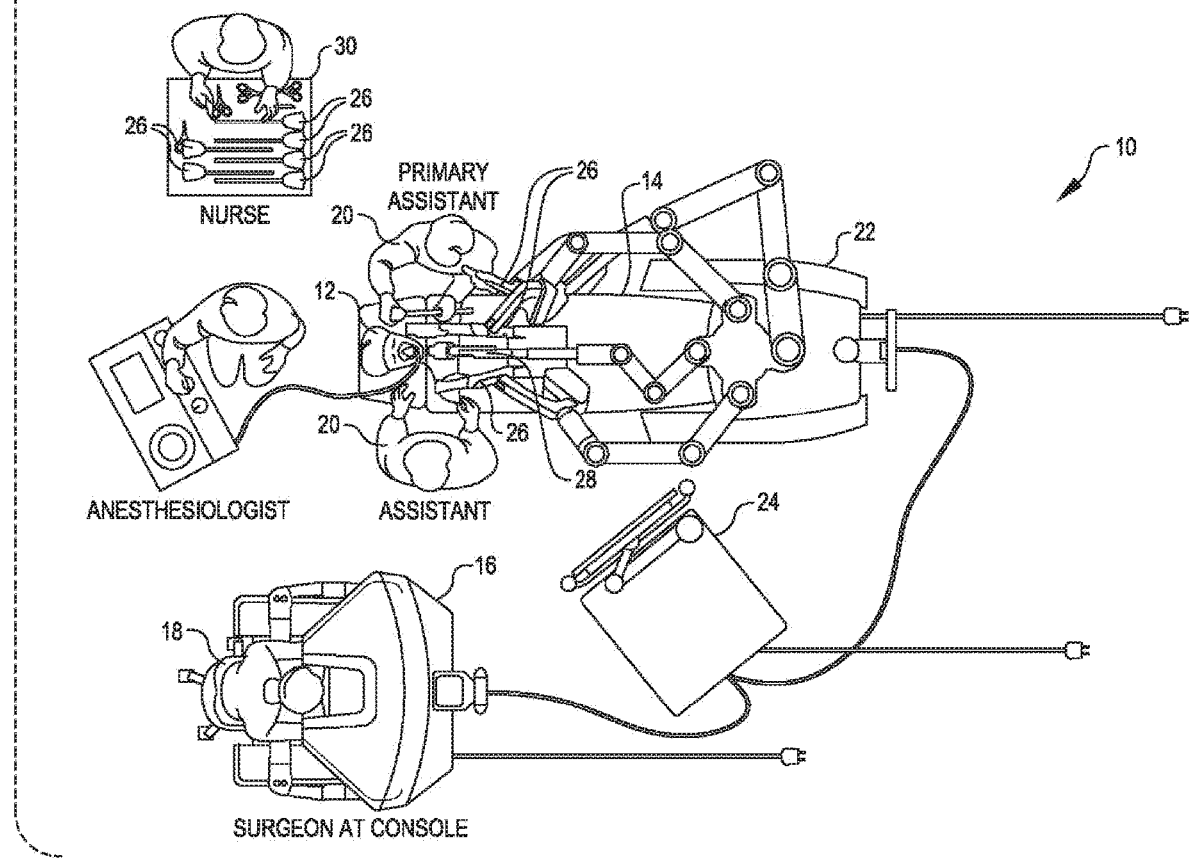
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
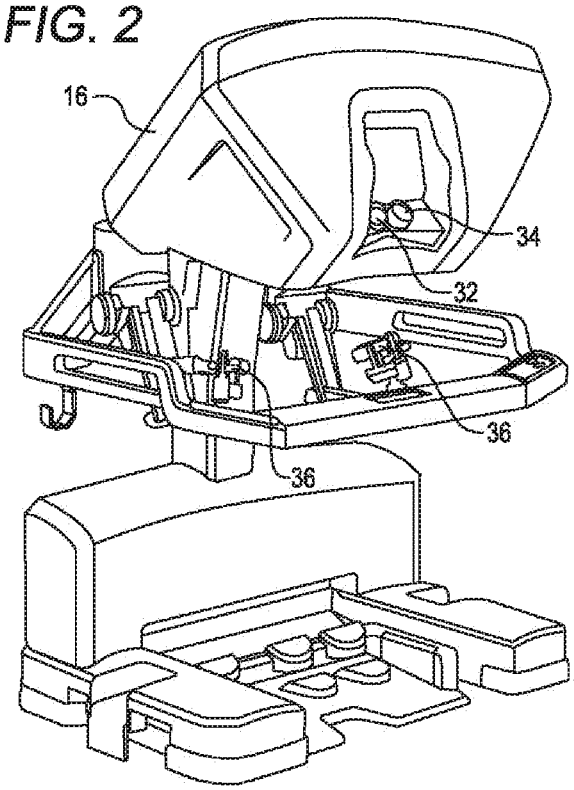
FIG. 2 is a view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
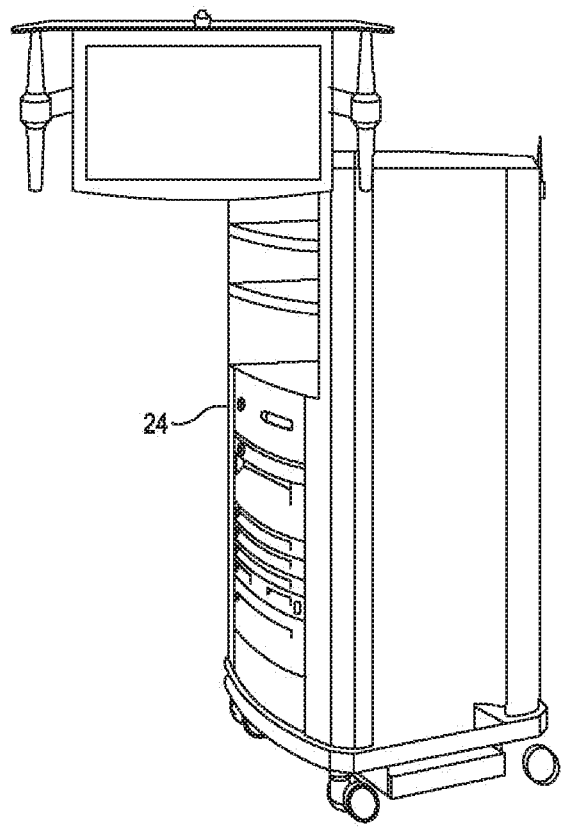
FIG. 3 is a view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

FIG. 4 diagrammatically illustrates the robotic surgery system 10. As discussed above, the Surgeon's Console 16 can be used by a Surgeon to control the Patient Side Cart 22 (Surgical Robot) during a minimally invasive procedure. The Patient Side Cart 22 can use an imaging device, such as a stereoscopic endoscope, to capture images of the procedure site and output the captured images to the Electronics Cart 24. As discussed above, the Electronics Cart 24 can process the captured images in a variety of ways prior to any subsequent display. For example, the Electronics Cart 24 can overlay the captured images with a virtual control interface prior to displaying the combined images to the Surgeon via the Surgeon's Console 16. The Patient Side Cart 22 can output the captured images for processing outside the Electronics Cart 24. For example, the Patient Side Cart 22 can output the captured images to a processor 38, which can be used to process the captured images. The images can also be processed by a combination the Electronics Cart 24 and the processor 38, which can be coupled together to process the captured images jointly, sequentially, and/or combinations thereof. One or more separate displays 40 can also be coupled with the processor 38 and/or the Electronics Cart 24 for local and/or remote display of images, such as images of the procedure site, or other related images.

Figure 6:
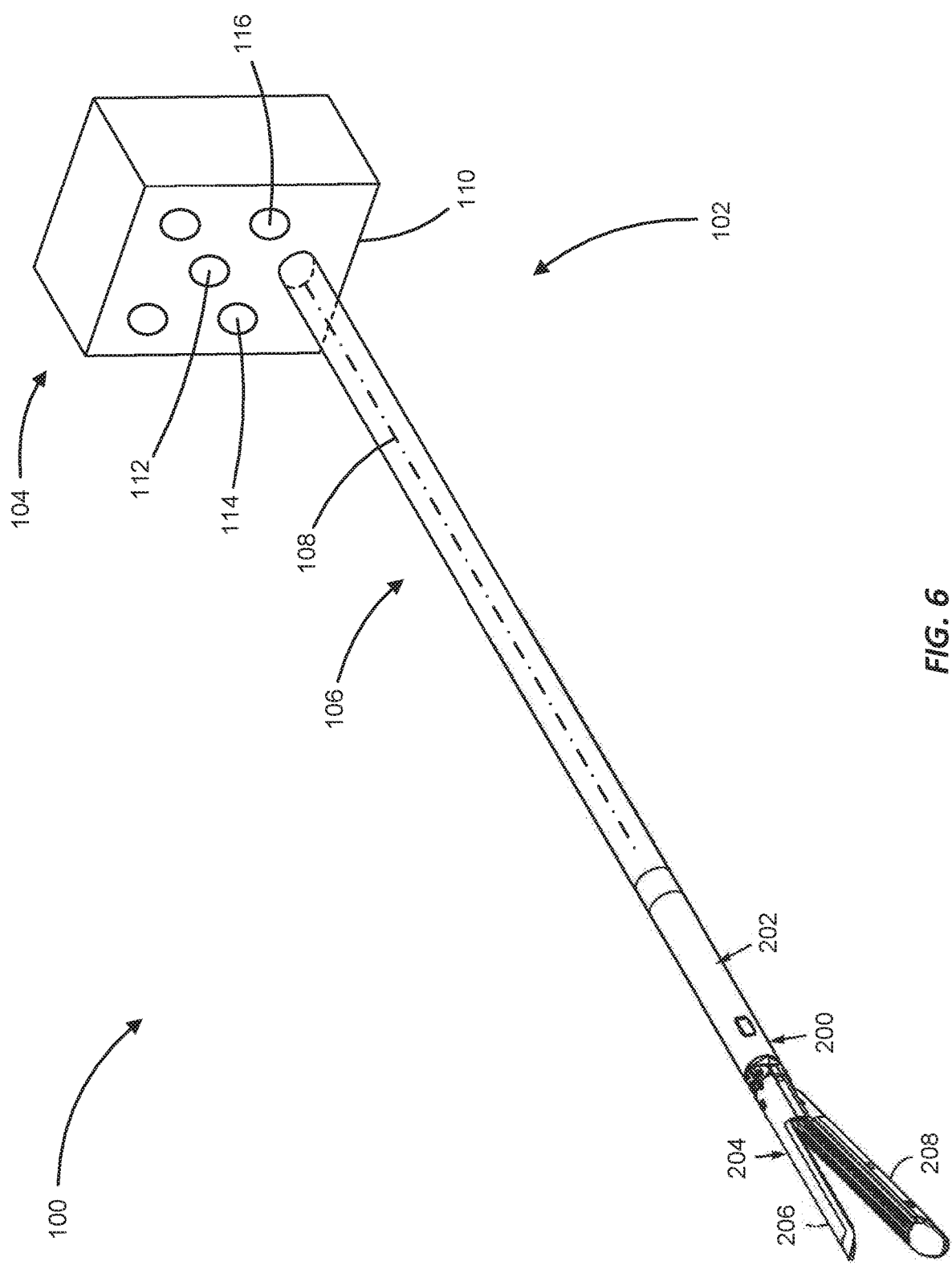
FIG. 6 is a view of a robotic surgery tool that includes a demountable stapler reload portion, in accordance with many embodiments.

FIG. 5 and FIG. 6 show a Patient Side Cart 22 and a surgical tool 100, respectively. The surgical tool 100 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Robotic Surgical Tool Configured to Use Hand-Held Stapler Reload

The surgical tool 100 includes a robotic surgical assembly 102 and a replaceable stapler reload 200 that is detachably coupled with the surgical assembly 102. In many embodiments, the stapler reload 200 is configured for use with an existing hand-held surgical stapler.

The robotic surgical assembly 102 is configured to be detachably mountable to a surgical robot (e.g., the patient side cart 22) for use in clamping, stapling, and cutting tissue with the stapler reload 200. The surgical assembly 102 is configured to mount to an instrument holder of the patient side cart 22. The surgical assembly 102 includes a proximal drive assembly 104 and a shaft assembly 106 mounted to the drive assembly 104 and extending distally from the drive assembly 104 along a shaft axis 108. The drive assembly includes a chassis 110, a roll input member 112 mounted to the chassis 110 and rotatable relative to the chassis 110 by a respective roll output member of the patient side cart 22, a pitch input member 114 mounted to the chassis 110 and rotatable relative to the chassis 110 by a respective pitch output member of the patient side cart 22, and a clamp/fire input member 116 mounted to the chassis 110 and rotatable relative to the chassis 110 by a respective clamp/fire output member of the patient side cart 22.

The stapler reload 200 is a single use replaceable assembly that is detachably mountable to the shaft assembly 106. The stapler reload 200 includes a proximal shaft assembly 202 and a stapler end effector 204. The proximal shaft assembly 202 is detachably mountable to a distal end of the shaft assembly 106. The end effector 204 is pivotally attached to a distal end of the proximal shaft assembly 202. The end effector 204 includes an upper jaw 206 and a stapler cartridge assembly 208. The stapler cartridge assembly 208 is pivotally mounted relative to the upper jaw 206 and can be actuated from an open position to a closed position to clamp tissue between the stapler cartridge assembly 208 and the upper jaw 206. The stapler cartridge assembly 208 includes an actuation input that is translatable distally to close the stapler cartridge 208 to clamp tissue between the stapler cartridge 208 and the upper jaw 206, to deploy staples from the stapler cartridge assembly 208, and to cut the stapled tissue. The deployed staples penetrate through tissue clamped between the stapler cartridge 208 and the upper jaw 206 and into contact with an anvil surface of the upper jaw 206 that forms ends of the staples to retain the staples in the stapled tissue.

Figure 7:
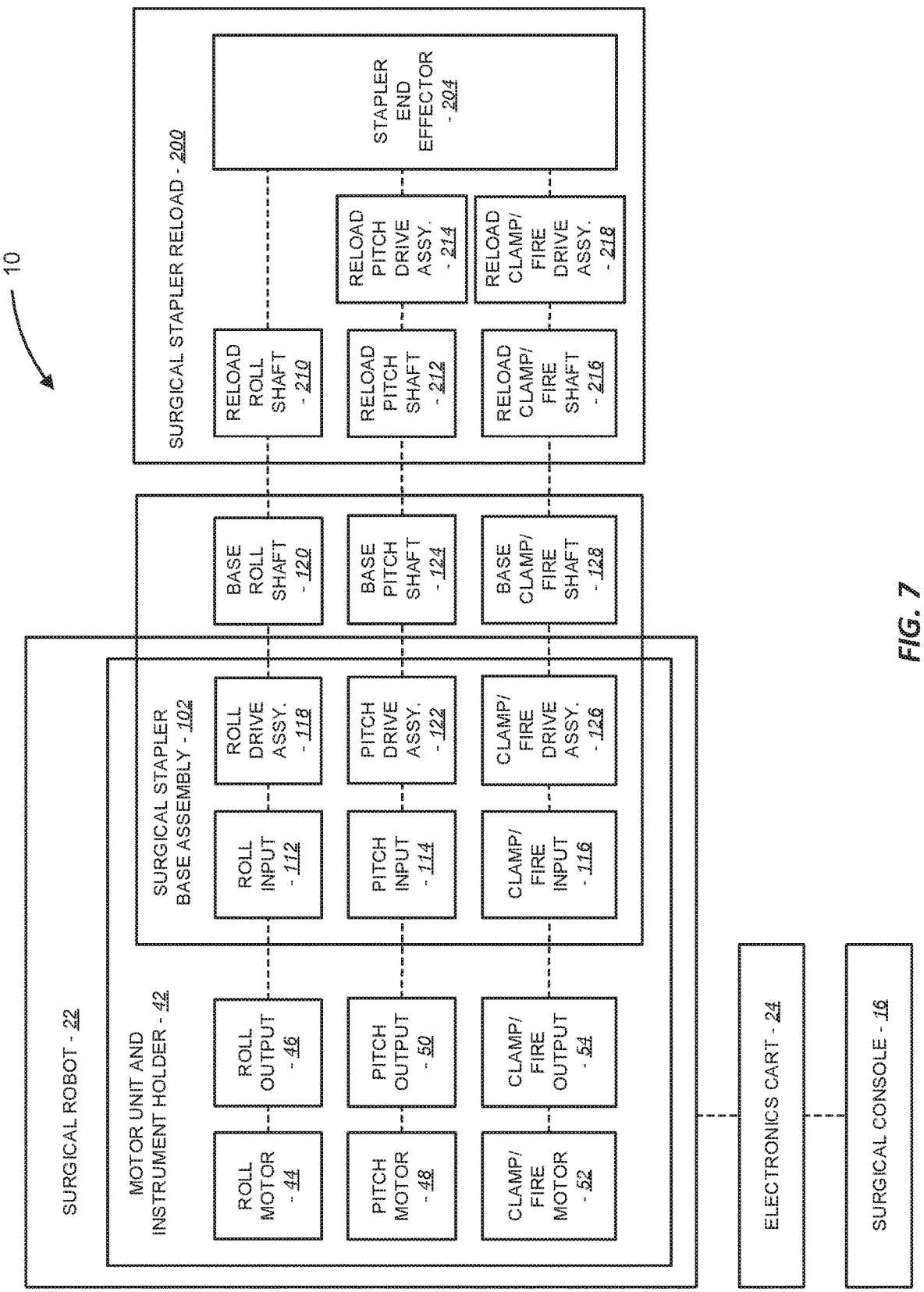
FIG. 7 is a simplified schematic diagram of a minimally invasive robotic surgery system including a surgical robot, a surgical stapler base assembly mounted to the surgical robot, and a surgical stapler reload mounted to the surgical stapler base assembly, in accordance with many embodiments.

FIG. 7 is a simplified schematic diagram of components of an embodiment of the Minimally Invasive Robotic Surgical (MIRS) system 10. The illustrated components of the robotic surgical system 10 include includes the surgical robot 22, the surgical stapler base assembly 102 mounted to the surgical robot 22, a surgical stapler reload 200 mounted to the surgical stapler base assembly 102, the electronics cart 24, and the surgical console 16.

The surgical robot 22 includes a motor unit and instrument holder 42 to which the surgical stapler base assembly 102 is detachably mountable. The motor unit and instrument holder 42 is operable to controllably actuate the surgical stapler base assembly 102 to controllably actuate the surgical stapler reload 200. The motor unit and instrument holder 42 includes a roll motor 44, a roll output 46 drivingly coupled with the roll motor 44, a pitch motor 48, a pitch output 50 drivingly coupled with the pitch motor 48, a clamp/fire motor 52, and a clamp/fire output 54 drivingly coupled with the clamp/fire motor 52. The roll motor 44 can be controllably operated to controllably rotate the roll output 46 relative to the motor unit and instrument holder 42. Similarly, the pitch motor 48 can be controllably operated to controllably rotate the pitch output 50 relative to the motor unit and instrument holder 42 and the clamp/fire motor 52 can be controllably operated to controllably rotate the clamp/fire output 54 relative to the motor unit and instrument holder 42.

The surgical stapler base assembly 102 is configured to actuate the surgical stapler reload 200 in response to actuation of the surgical stapler base assembly 102 by the motor unit and instrument holder 42. The base assembly 102 includes the roll input 112, a roll drive assembly 118, a base roll shaft 120, the pitch input 114, a pitch drive assembly 122, a base pitch shaft 124, the clamp/fire input 116, a clamp/fire drive assembly 126, and a base clamp/fire shaft 128. When the base assembly 102 is mounted to the motor unit and instrument holder 42, the roll input 112 is drivingly coupled with the roll output 46 so that rotation of the roll output 46 generates matching rotation of the roll input 112, the pitch input 114 is drivingly coupled with the pitch output 50 so that rotation of the pitch output 50 generates matching rotation of the pitch input 114, and the clamp/fire input 116 is drivingly coupled with the clamp/fire output 54 so that rotation of the clamp/fire output 54 generates matching rotation of the clamp/fire input 116. The base roll shaft 120 is drivingly coupled with the roll input 112 via the roll drive assembly 118 so that rotation of the roll input 112 generates a corresponding rotation of the base roll shaft 120 around the shaft axis 108. The base pitch shaft 124 is drivingly coupled with the pitch input 114 via the pitch drive assembly 122 so that rotation of the pitch input 114 generates a corresponding translation of the base pitch shaft 124 along the shaft axis 108. The base clamp/fire shaft 128 is drivingly coupled with the clamp/fire input 116 via the clamp/fire drive assembly 126 so that rotation of the clamp/fire input 116 generates a corresponding translation of the base clamp/fire shaft 128 along the shaft axis 108.

The surgical stapler reload 200 includes a reload roll shaft 210, a reload pitch shaft 212, a reload pitch drive assembly 214, a reload clamp/fire shaft 216, a reload clamp/fire drive assembly 218, and the stapler end effector 204. When the stapler reload 200 is mounted to the base assembly 102, the reload roll shaft 210 is coupled to the base roll shaft 120 so that the reload roll shaft 210 rotates with the base roll shaft 120 around the shaft axis 108, the reload pitch shaft 212 is coupled with the base pitch shaft 124 so that the reload pitch shaft 212 translates with the base pitch shaft 124 along the shaft axis 108, and the reload clamp/fire shaft 216 is coupled with the base clamp/fire shaft 128 so that the reload clamp/fire shaft 216 translates with the base clamp/fire shaft 128 along the shaft axis 108. The stapler end effector 204 can be pivotally mounted to the reload roll shaft 210. The stapler end effector 204 is drivingly coupled with the reload pitch shaft 212 via the reload pitch drive assembly 214 so that translation of the reload pitch shaft 212 along the shaft axis 108 reorients the stapler end effector 204 relative to the reload roll shaft 210. The stapler end effector 204 is also drivingly coupled with the reload clamp/fire shaft 216 via the reload clamp/fire assembly 218 so that translation of the reload clamp/fire shaft 216 along the shaft axis 108 can be used to actuate the stapler cartridge assembly 208 to clamp tissue between the stapler cartridge assembly 208 and the upper jaw 206, to deploy staples from the stapler cartridge assembly 208, and to cut the stapled tissue.

Figure 8:
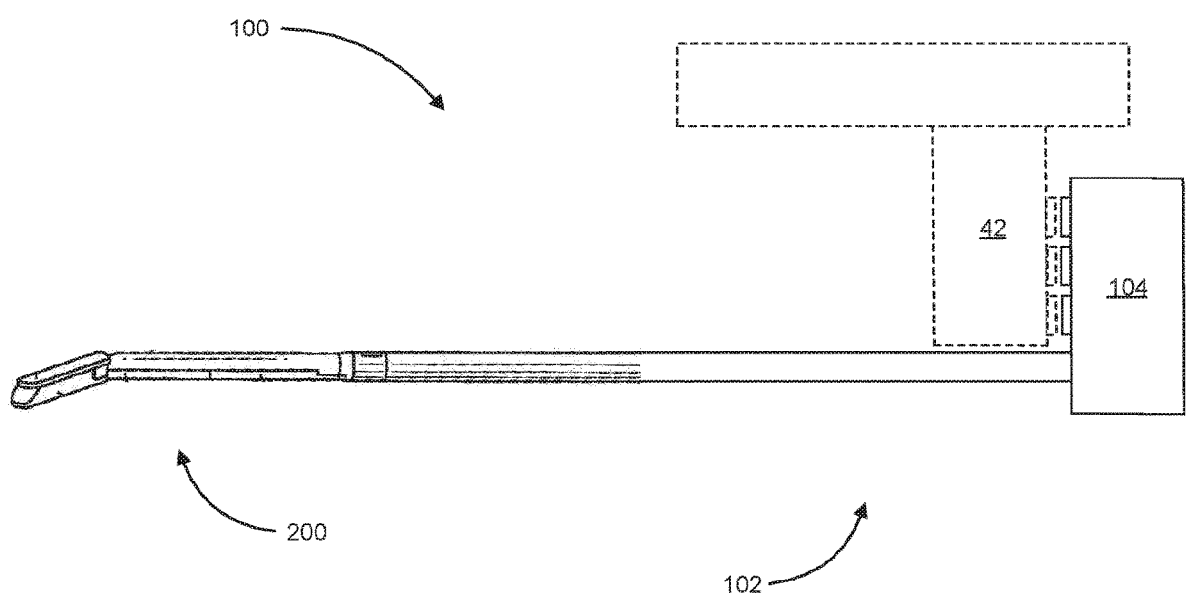
FIG. 8 is a side view of a surgical stapler base assembly mounted to a surgical robot, and a surgical stapler reload mounted to the surgical stapler base assembly, in accordance with many embodiments.

FIG. 8 shows a side view of the surgical tool 100 with the drive assembly 104 mounted to the motor unit and instrument holder 42. In the illustrated configuration, the motor unit and instrument holder 42 is operable to controllably rotate the roll output 46, the pitch output 50, and the clamp/fire output 54 to controllably actuate the surgical base assembly 102, which thereby controllably articulates/actuate the stapler reload 200.

Figure 9:
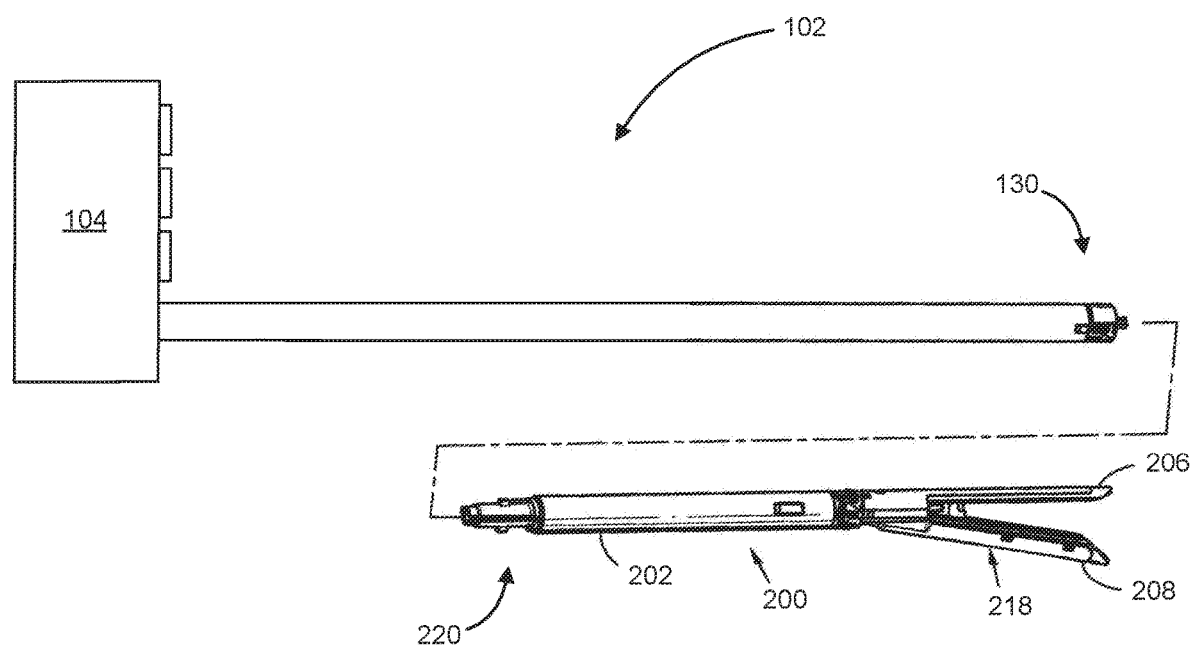
FIG. 9 is a side view of the surgical stapler base assembly and the surgical stapler reload of FIG. 8 showing the surgical stapler reload separated from the surgical stapler base assembly, in accordance with many embodiments.

FIG. 9 is a side view of the surgical stapler base assembly 102 and the surgical stapler reload 200 showing the surgical stapler reload 200 separated from the surgical stapler base assembly 102. As discussed in more detail with respect to FIG. 10, the base assembly 102 includes a distal portion 130 configured to receive and drivingly couple with a proximal portion 220 of the stapler reload 200.

Figure 10:
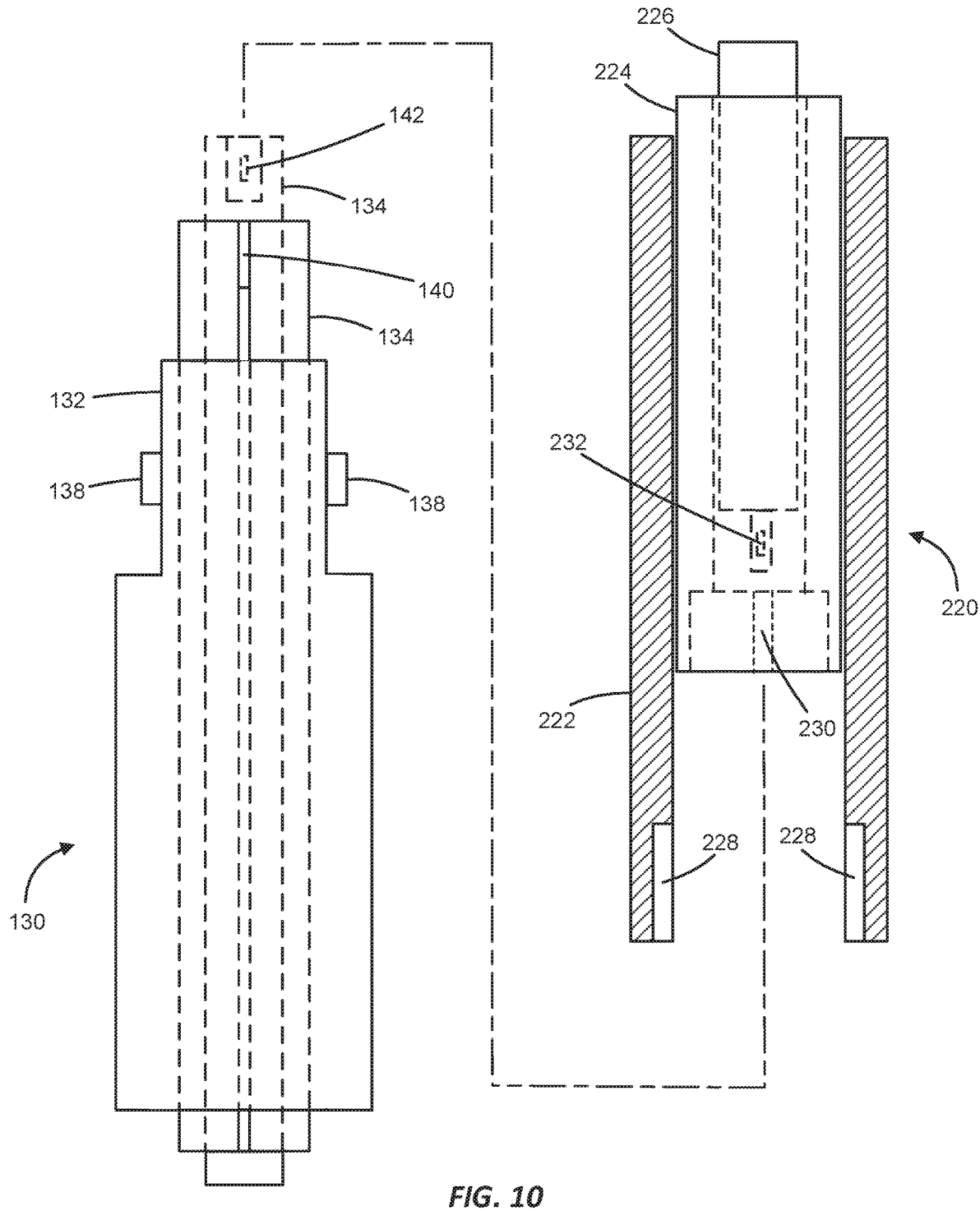
FIG. 10 is a simplified schematic side view of a distal end of the surgical stapler base assembly and a proximal end of the surgical stapler reload of FIG. 8 showing the surgical stapler reload separated from the surgical stapler base assembly, in accordance with many embodiments.

FIG. 10 is a simplified schematic side view of the distal portion 130 of the surgical stapler base assembly 102 and the proximal portion 220 of the stapler reload 200. The distal portion 130 of the base assembly 102 includes a distal portion 132 of the base roll shaft 120, a distal portion 134 of the base pitch shaft 124, and a distal portion 136 of the base clamp/fire shaft 128. The proximal portion 220 of the stapler reload 200 includes a proximal portion 222 of the reload roll shaft 210, a proximal portion 224 of the reload pitch shaft 212, and a proximal portion 226 of the reload clamp/fire shaft 216. In the illustrated embodiment, the proximal portion 132 of the base roll shaft 120 includes protruding features 138 configured to be inserted into slots 228 in the reload roll shaft 210 to rotationally tie the reload roll shaft 210 to the base roll shaft 120. In many embodiments, a retention mechanism prevents inadvertent separation of the stapler reload 200 from the base assembly 102. In the illustrated embodiment, the distal portion 134 of the base pitch shaft 124 includes a spring-loaded coupling feature 140 configured to be received and engage a shaped slot 230 in the proximal portion 224 of the reload pitch shaft 212 to constrain the reload pitch shaft 212 to translate with the base pitch shaft 124 along the shaft axis 108. In a similar manner, in the illustrated embodiment the distal portion 136 of the base clamp/fire shaft 128 includes a coupling feature 142 configured to engage a coupling feature 232 of the reload clamp/fire shaft 216 to constrain the reload clamp/fire shaft 216 to translate with the base clamp/fire shaft 128 along the shaft axis 108.

Figure 11:
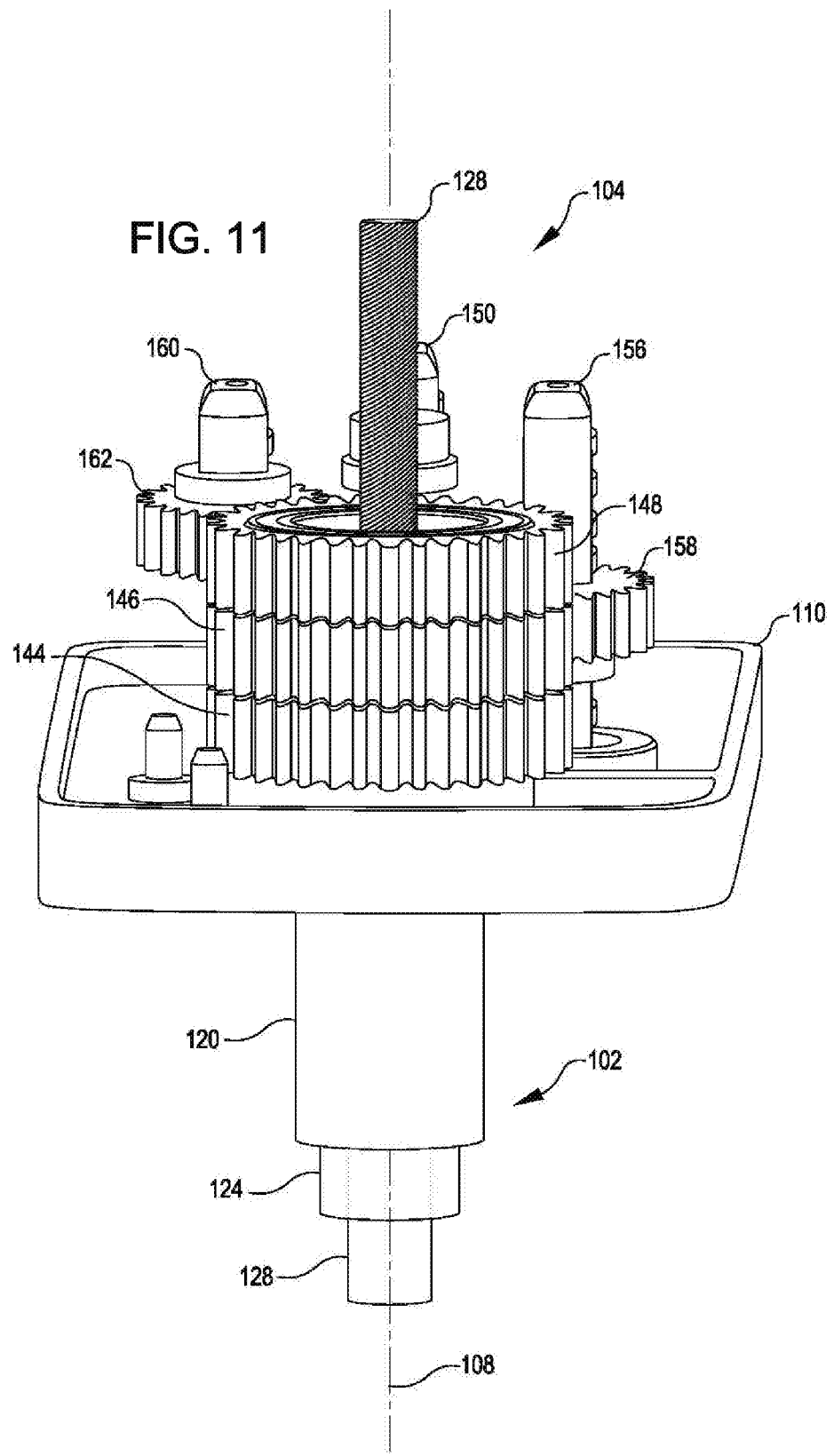
FIG. 11 and FIG. 12 illustrate components of a drive assembly of the surgical stapler base assembly of FIG. 8, in accordance with many embodiments.
Figure 12:
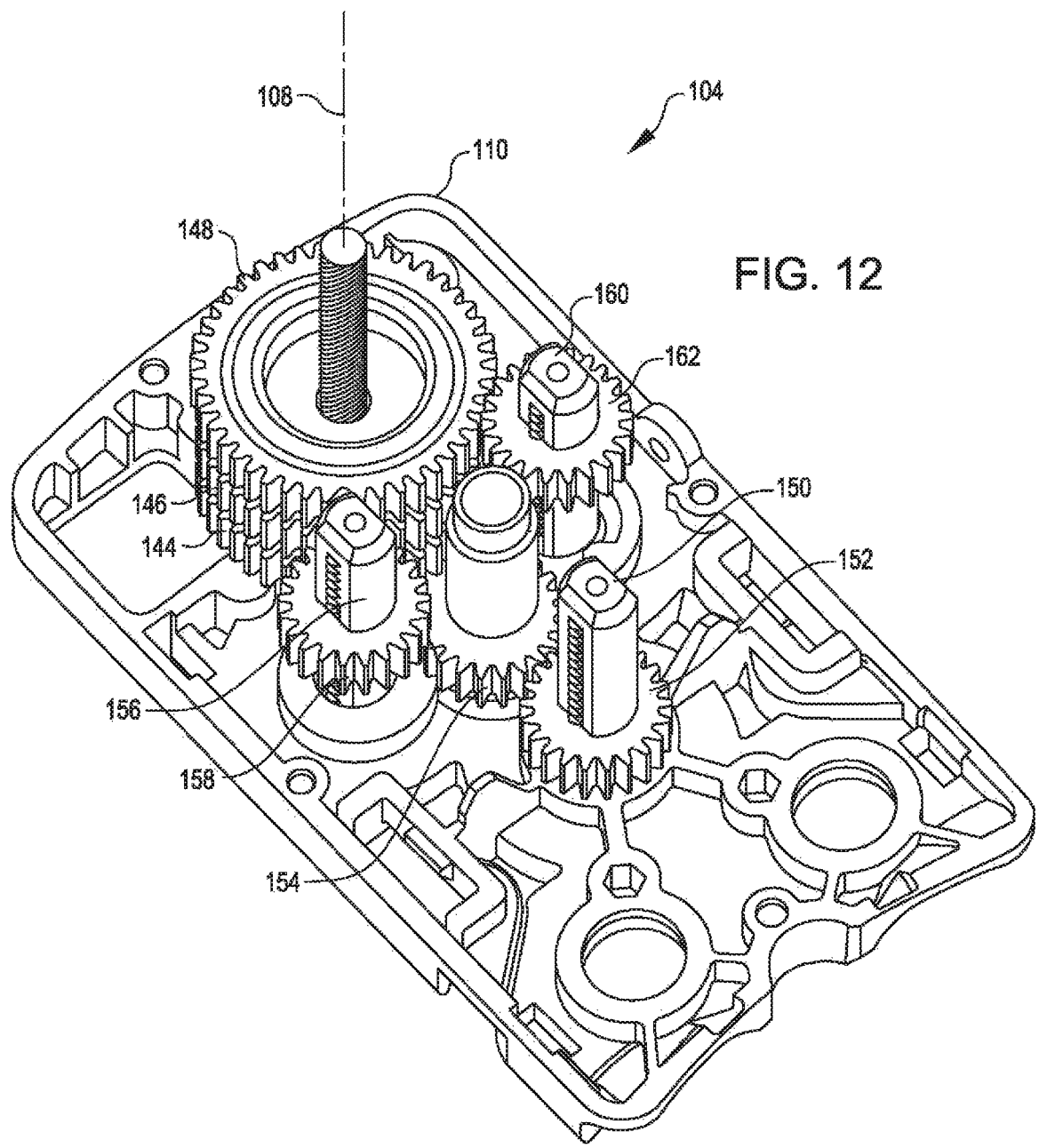

FIG. 11 and FIG. 12 illustrate components of the drive assembly 100, which is used drivingly couple the base roll shaft 120 with the roll input 112, the base pitch shaft 124 with the pitch input 114, and the base clamp/fire shaft 128 with the clamp/fire input 116. The drive assembly 104 includes the chassis 110, a roll output gear 144, a pitch output gear 146, a clamp/fire output gear 148, a roll input shaft 150, a roll input gear 152, a roll idler gear 154, a pitch input shaft 156, a pitch input gear 158, a clamp/fire input shaft 160, and a clamp/fire input gear 162. As described in more detail herein, the roll output gear 144, the pitch output gear 146, and the clamp/fire output gear 148 are coaxially mounted to rotate about the shaft axis 108. The roll output gear 144 is rotationally tied to the base roll shaft 120 so that the base roll shaft 120 is rotated by rotating the roll output gear 144. The base pitch shaft 124 is interfaced with the pitch output gear 146 via a screw thread so that the base pitch shaft 124 is translated along the shaft axis 108 via rotation of the pitch output gear 146. The base clamp/fire shaft 128 is interfaced with the clamp/fire output gear 148 via a screw thread so that the base clamp/fire shaft 128 is translated along the shaft axis 108 via rotation of the clamp/fire output gear 148. The roll input gear 152 is mounted and rotationally tied to the roll input shaft 150, which is rotationally tied to the roll input 112. The roll input gear 152 includes external gear teeth, which engage external gear teeth of the roll idler gear 154 to rotate the roll idler gear 154 in response to rotation of the roll input 112. The external teeth of the roll idler gear 154 engage external gear teeth of the roll output gear 144 to rotate the roll output gear 144 in response to rotation of the roll idler gear 154. The pitch input gear 154 is mounted and rotationally tied to the pitch input shaft 156, which is rotationally tied to the pitch input 114. The pitch input gear 158 includes external gear teeth, which engage external gear teeth of the pitch output gear 146 to rotate the pitch output gear 146 in response to rotation of the pitch input gear 158. The clamp/fire input gear 162 is mounted and rotationally tied to the clamp/fire input shaft 160, which is rotationally tied to the clamp/fire input 116. The clamp/fire input gear 162 includes external gear teeth, which engage external gear teeth of the claim/fire output gear 148 to rotate the clamp/fire output gear 148 in response to rotation of the clamp/fire input gear 162.

Figure 13B:
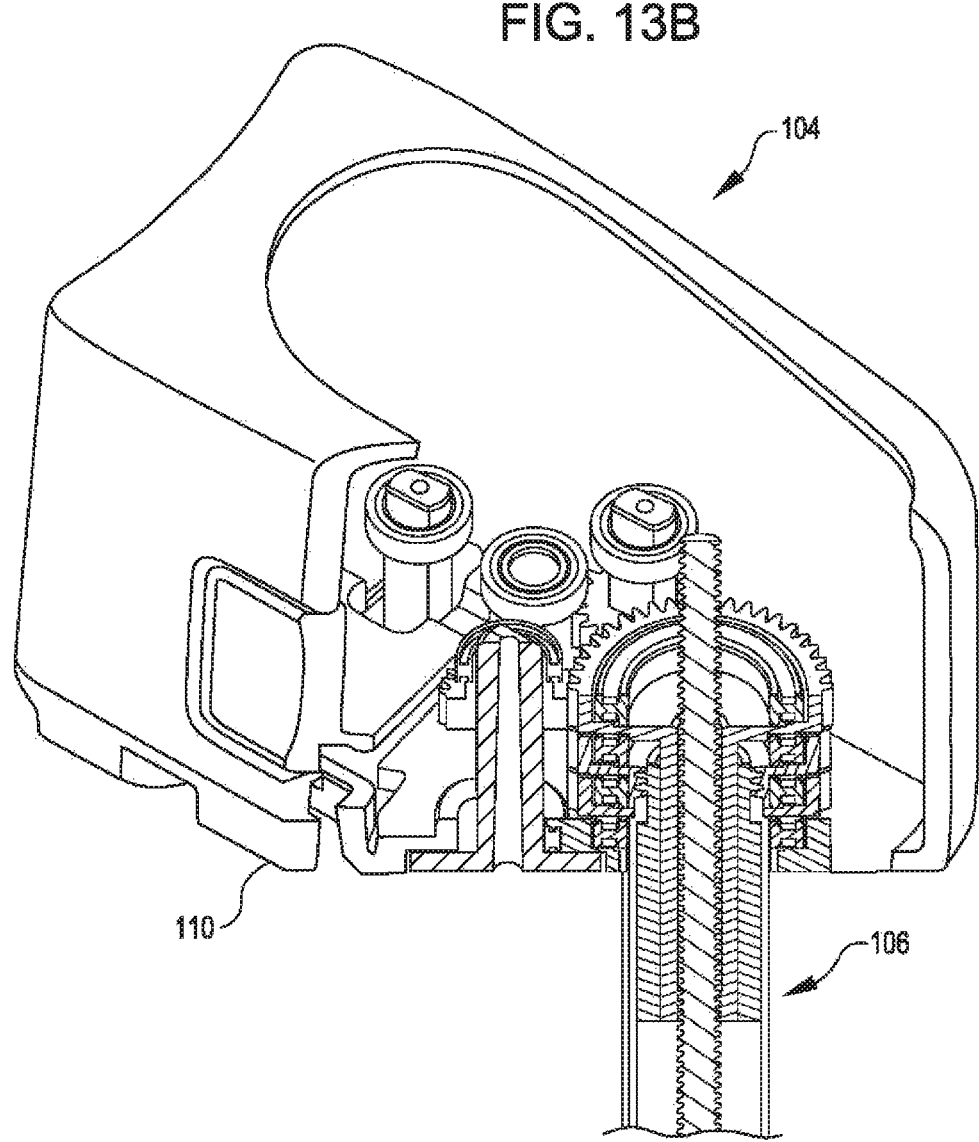

FIG. 13A and FIG. 13B illustrate components of the drive assembly 104 of the surgical stapler base assembly 102 for generating translation of the base claim/fire shaft 128. In the illustrated embodiment, the clamp/fire input 116 and the clamp/fire input shaft 160 form an integral component. In FIG. 13A, the clamp/fire input 116, the clamp fire input shaft 160, the clamp/fire input gear 162, the clamp/fire output gear 148, and the base clamp/fire shaft 128 are shown in isolation to better illustrate how translation of the base clamp/fire shaft 128 along the shaft axis 108 is generated by rotation of the clamp/fire input 116. Specifically, rotation of the clamp/fire input 116 relative to the chassis 110 rotates the clamp/fire input shaft 160 relative to the chassis 110, which rotates the clamp/fire input gear 162 relative to the chassis 110, which rotates the clamp/fire output gear 148 relative to the chassis 110. In many embodiments, the base clamp/fire shaft 128 is constrained to rotate with the base roll shaft 120 so that rotation of the clamp/fire output gear 148 produces rotation of the clamp/fire output gear 148 relative to the base clamp/fire shaft 128 absent matching rotation of the base roll shaft 120 and the clamp/fire output gear 148. The clamp/fire output gear 148 and the base clamp/fire shaft 128 are interfaced via a clamp/fire screw thread interface 164. Rotation of the clamp/fire output gear 148 relative to the base clamp/fire shaft 128 produces translation of the base clamp/fire shaft 128 along the shaft axis 108 via the clamp/fire screw thread interface 164.

Figure 14B:
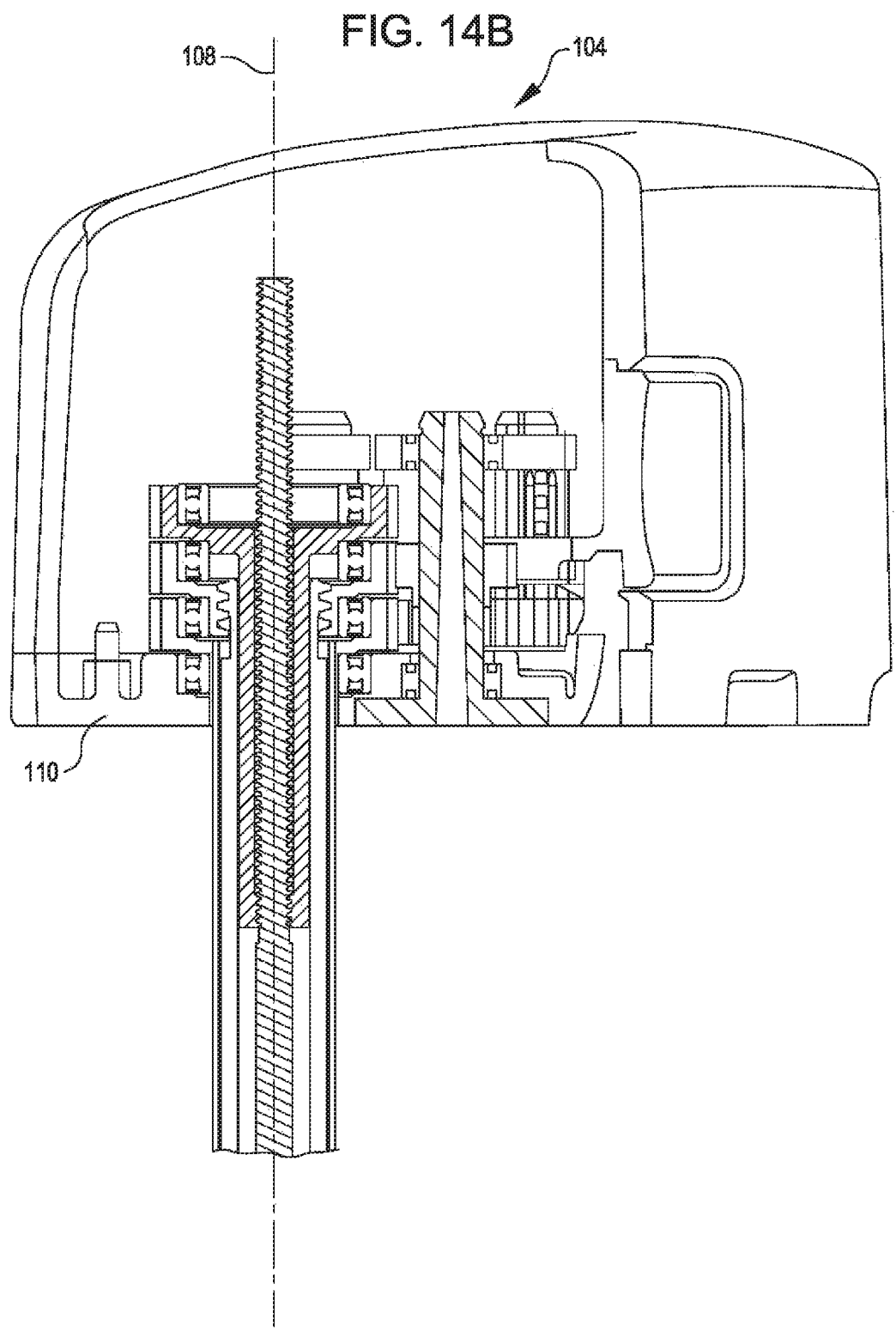

FIG. 14A and FIG. 14B illustrate components of the drive assembly 104 of the surgical stapler base assembly 102 for generating translation of the base pitch shaft 124. In FIG. 13A, the pitch input 114, the pitch input shaft 156, the pitch input gear 158, the pitch output gear 146, and the base pitch shaft 124 are shown in isolation to better illustrate how translation of the base pitch shaft 124 along the shaft axis 108 is generated by rotation of the pitch input 114. Specifically, rotation of the pitch input 114 relative to the chassis 110 rotates the pitch input shaft 156 relative to the chassis 110, which rotates the pitch input gear 158 relative to the chassis 110, which rotates the pitch output gear 146 relative to the chassis 110. In many embodiments, the base pitch shaft 124 is constrained to rotate with the base roll shaft 120 so that rotation of the pitch output gear 146 produces rotation of the pitch output gear 146 relative to the base pitch shaft 124 absent matching rotation of the base roll shaft 120 and the pitch output gear 146. The pitch output gear 146 and the base pitch shaft 124 are interfaced via a pitch screw thread interface 166. Rotation of the pitch output gear 146 relative to the base pitch shaft 124 produces translation of the base pitch shaft 124 along the shaft axis 108 via the pitch screw thread interface 166.

Figure 16:
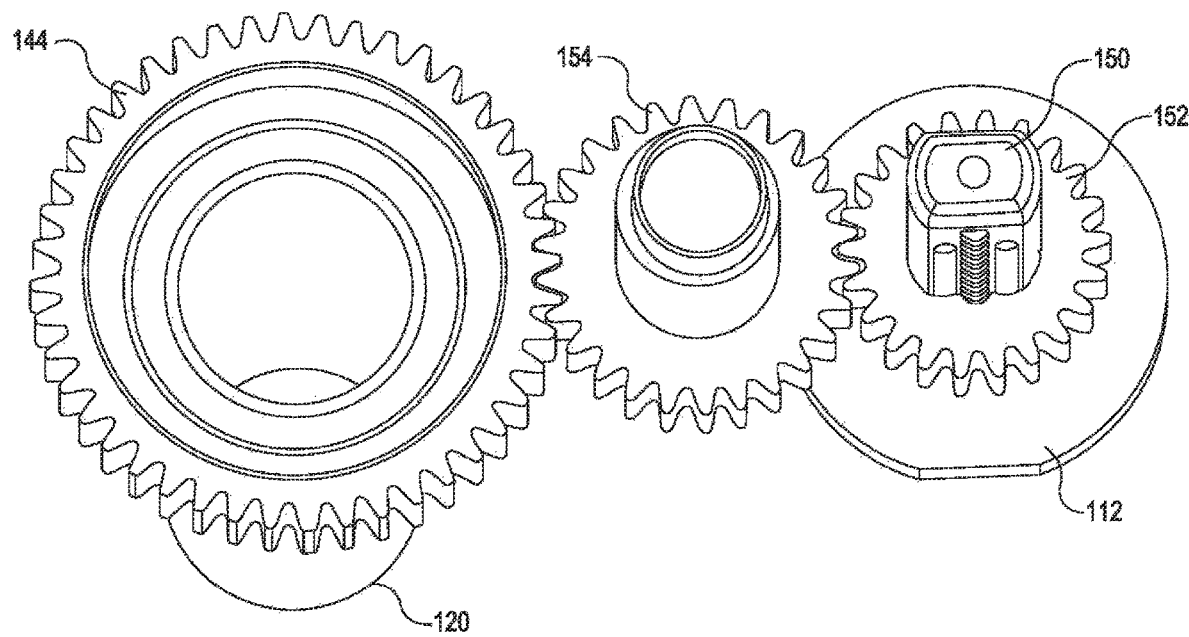

FIG. 15A, FIG. 15B, and FIG. 16 illustrate components of the drive assembly 104 of the surgical stapler base assembly 102 for generating rotation of the base roll shaft 120. In FIG. 15A, the roll input 112, the roll input shaft 150, the roll input gear 152, the roll idler gear 154, the roll output gear 144, and the base roll shaft 120 are shown in isolation to better illustrate how rotation of the base roll shaft 120 around the shaft axis 108 is generated by rotation of the roll input 112. Specifically, rotation of the roll input 112 relative to the chassis 110 rotates the roll input shaft 150 relative to the chassis 110, which rotates the roll input gear 152 relative to the chassis 110, which rotates the roll idler gear 154 relative to the chassis 110, which rotates the roll output gear 144 relative to the chassis 110, which rotates the base roll shaft 120 relative the chassis 110.

FIG. 17 is a cross-sectional view through the output gears 144, 146, 148 illustrating roller bearings used to mount the output gears 144, 146, 148 to the chassis 110 and constrain rotation of the output gears 144, 146, 148 to rotation around the shaft axis 108. The roller bearings used to mount the output gears 144, 146, 148 include a shaft bearing 168, a roll output gear bearing 170, a pitch output gear bearing 172, and a clamp/fire output gear bearing 174. The shaft bearing 168 is mounted to the chassis 110 so that an outer race of the shaft bearing 168 is interfaced the chassis 110. The roll output gear 144 is mounted to the shaft bearing 168 so that an inner race of the shaft bearing 168 is interfaced with the roll output gear 144. The roll output gear bearing 170 is mounted inside a recess in the roll output gear 144 so that an outer race of the roll output gear bearing 170 is interfaced with the roll output gear 144. The pitch output gear 146 is mounted to the roll output gear bearing 170 so that an inner race of the roll output gear bearing 170 is interfaced with the pitch output gear 146. The pitch output gear bearing 172 is mounted inside a recess in the pitch output gear 146 so that an outer race of the pitch output gear bearing 172 is interfaced with the pitch output gear 146. The clamp/fire output gear 148 is mounted to the pitch output gear bearing 172 so that an inner race of the pitch output gear bearing 172 is interfaced with the clamp/fire output gear 148. The clamp/fire output gear bearing 174 is mounted inside a recess in the clamp/fire output gear 148 so that an outer race of the clamp/fire output gear bearing 174 is interfaced with the clamp/fire output gear 148. Although not shown in FIG.

17, an inner race of the clamp/fire gear bearing 174 is interfaced with an upper chassis, which is coupled with the chassis 110 and provides additional support for the output gears 144, 146, 148.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A robotic surgical assembly, comprising:
  a drive assembly detachably mountable to a surgical robot, the drive assembly comprising:
    a chassis;
    a roll input configured to drivingly couple with a roll output of the surgical robot;
    a pitch input configured to drivingly couple with a pitch output of the surgical robot; and
    a clamp/fire input configured to drivingly couple with a clamp/fire output of the surgical robot; and
  a shaft assembly mounted to the drive assembly and configured to detachably couple with a stapler reload assembly,
  wherein the shaft assembly comprises:
    a shaft axis, the shaft assembly being elongated along the shaft axis;
    a roll shaft;
    a roll output gear attached to the roll shaft and constrained to rotate around the shaft axis, the roll output gear drivingly coupled with the roll input so that rotation of the roll input rotates the roll shaft around the shaft axis;
    a pitch shaft;
    a pitch output gear drivingly coupled with the pitch shaft via a first screw thread interface configured to convert rotation of the pitch output gear into translation of the pitch shaft along the shaft axis, the pitch output gear constrained to rotate about the shaft axis and drivingly coupled with the pitch input so that rotation of the pitch input translates the pitch shaft along the shaft axis;
    a clamp/fire shaft; and
    a clamp/fire output gear drivingly coupled with the clamp/fire shaft via a second screw thread interface configured to convert rotation of the clamp/fire output gear into translation of the clamp/fire shaft along the shaft axis, the clamp/fire output gear constrained to rotate about the shaft axis and drivingly coupled with the clamp/fire input so that rotation of the clamp/fire input translates the clamp/fire shaft along the shaft axis;
  wherein in a coupled state of the shaft assembly with the stapler reload assembly:
    the roll shaft is configured to engage with a reload roll shaft of the stapler reload assembly to which an end effector of the stapler reload assembly is pivotably mounted,
    the pitch shaft is configured to engage with a reload pitch shaft of the stapler reload assembly translatable along the shaft axis to reorient the end effector relative to the reload roll shaft, and
    the clamp/fire shaft is engaged with a reload clamp/fire shaft of the stapler reload assembly translatable along the shaft axis to actuate the end effector to clamp and staple tissue.

2. The robotic surgical assembly of claim 1, wherein:
  the roll shaft has a roll shaft lumen extending along the shaft axis;
  the pitch shaft is accommodated within the roll shaft lumen and constrained to rotate with the roll shaft around the shaft axis;
  the pitch shaft has a pitch shaft lumen extending along the shaft axis; and
  the clamp/fire shaft is accommodated within the pitch shaft lumen and constrained to rotate with the roll shaft around the shaft axis.

3. The robotic surgical assembly of claim 1, wherein the drive assembly comprises:
  a shaft bearing having an outer race interfaced with the chassis and an inner race interfaced with the roll output gear, the shaft bearing constraining the roll output gear to rotation around the shaft axis;

a roll output gear bearing having an outer race interfaced with the roll output gear and an inner race interfaced with the pitch output gear, the roll output gear bearing constraining the pitch output gear to rotation around the shaft axis; and a pitch output gear bearing having an outer race interfaced with the pitch output gear and an inner race interfaced with the clamp/fire output gear, the pitch output gear bearing constraining the clamp/fire output gear to rotation around the shaft axis.

4. The robotic surgical assembly of claim 3, wherein the drive assembly comprises:
   an upper chassis supported by the chassis; and
   a clamp/fire output gear bearing having an inner race interfaced with the upper chassis and an outer race interfaced with the clamp/fire output gear.

5. The robotic surgical assembly of claim 4, wherein the upper chassis is detachably mountable to the chassis.

6. The robotic surgical assembly of claim 1, wherein the drive assembly comprises:
   a clamp/fire input shaft rotationally coupled with the clamp/fire input;
   a clamp/fire input gear rotationally coupled with the clamp/fire input shaft, the clamp/fire input gear having external gear teeth drivingly engaging external gear teeth of the clamp/fire output gear; and
   clamp/fire input shaft bearings, each of the clamp/fire input shaft bearings having an outer race interfaced with the chassis and an inner race interfaced with the clamp/fire input shaft.

7. The robotic surgical assembly of claim 1, wherein the drive assembly comprises:
   a pitch input shaft rotationally coupled with the pitch input;
   a pitch input gear rotationally coupled with the pitch input shaft, the pitch input gear having external gear teeth drivingly engaging external gear teeth of the pitch output gear; and
   pitch input shaft bearings, each of the pitch input shaft bearings having an outer race interfaced with the chassis and an inner race interfaced with the pitch input shaft.

8. The robotic surgical assembly of claim 1, wherein the drive assembly comprises:
   a roll input shaft rotationally coupled with the roll input;
   roll input shaft bearings, each of the roll input shaft bearings having an outer race interfaced with the chassis and an inner race interfaced with the roll input shaft;
   a roll input gear rotationally coupled with the roll input shaft; and
   an idler gear having external teeth drivingly engaged by external teeth of the roll input gear and drivingly engaging external teeth of the roll output gear.

9. A surgical system, comprising:
   a drive assembly detachably mountable to a manipulator, the drive assembly comprising:
      a chassis;
      a roll input rotatably coupled to the chassis and configured to drivingly couple with a roll output of the manipulator;
      a pitch input rotatably coupled to the chassis and configured to drivingly couple with a pitch output of the manipulator; and
      a clamp/fire input rotatably coupled to the chassis and configured to drivingly couple with a clamp/fire output of the manipulator; and
   a shaft assembly extending along a shaft axis and coupled to the drive assembly, the shaft assembly comprising:
      a roll shaft;
      a roll output gear attached to the roll shaft and constrained to rotate about the shaft axis, the roll output gear drivingly coupled with the roll input so that rotation of the roll input rotates the roll shaft around the shaft axis;
      a pitch shaft;
      a pitch output gear drivingly coupled with the pitch shaft via a first screw thread interface configured to convert rotation of the pitch output gear into translation of the pitch shaft along the shaft axis, the pitch output gear constrained to rotate about the shaft axis and drivingly coupled with the pitch input so that rotation of the pitch input translates the pitch shaft along the shaft axis;
      a clamp/fire shaft; and
      a clamp/fire output gear drivingly coupled with the clamp/fire shaft via a second screw thread interface configured to convert rotation of the clamp/fire output gear into translation of the clamp/fire shaft along the shaft axis, the clamp/fire output gear constrained to rotate about the shaft axis and drivingly coupled with the clamp/fire input so that rotation of the clamp/fire input translates the clamp/fire shaft along the shaft axis;
      wherein the roll shaft, the pitch shaft, and the clamp/fire shaft are concentric about the shaft axis.

10. The system of claim 9, wherein:
    the roll shaft comprises a tubular shaft defining a roll shaft lumen; and
    the pitch shaft is received within the roll shaft lumen.

11. The system of claim 9, wherein:
    the pitch shaft comprises a tubular shaft defining a pitch shaft lumen; and
    the clamp/fire shaft is received within the pitch shaft lumen.

12. The system of claim 9, wherein the pitch shaft and the clamp/fire shaft are constrained to rotate with rotation of the roll shaft.

13. The system of claim 9, wherein the drive assembly further comprises:
    a clamp/fire input shaft rotationally coupled with the clamp/fire input; and
    a clamp/fire input gear rotationally coupled with the clamp/fire input shaft, the clamp/fire input gear having external gear teeth drivingly engaging external gear teeth of the clamp/fire output gear.

14. The system of claim 9, wherein the drive assembly further comprises:
    a pitch input shaft rotationally coupled with the pitch input; and
    a pitch input gear rotationally coupled with the pitch input shaft, the pitch input gear having external gear teeth drivingly engaging external gear teeth of the pitch output gear.

15. The system of claim 9, wherein the drive assembly further comprises: a roll input shaft rotationally coupled with the roll input;
    a roll input gear rotationally coupled with the roll input shaft; and an idler gear having external teeth drivingly engaged by external teeth of the roll input gear and drivingly engaging external teeth of the roll output gear.

* * * * *